(12) United States Patent
Olson

(10) Patent No.: US 6,533,959 B2
(45) Date of Patent: Mar. 18, 2003

(54) BROMINATED MATERIALS

(75) Inventor: David B. Olson, May Township, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 0 days.

(21) Appl. No.: 10/017,622

(22) Filed: Dec. 14, 2001

(65) Prior Publication Data

US 2002/0123590 A1 Sep. 5, 2002

Related U.S. Application Data

(62) Division of application No. 09/402,850, filed on Oct. 7, 1999, now Pat. No. 6,359,170.

(51) Int. Cl.[7] ........................ C09K 3/00; C07C 69/653
(52) U.S. Cl. ................................. 252/182.13; 560/221
(58) Field of Search ................................. 560/221, 223; 526/328; 252/182.13

(56) References Cited

U.S. PATENT DOCUMENTS

| 2,448,767 A | 9/1948 | Carlson |
| 3,817,913 A | 6/1974 | Gaenzler et al. |
| 4,975,223 A | 12/1990 | Doi et al. |
| 5,290,892 A | 3/1994 | Namdaran et al. |

FOREIGN PATENT DOCUMENTS

| EP | 0 485 197 A1 | 5/1992 |
| JP | 62-106050 | 5/1987 |
| JP | 62-106912 | 5/1987 |
| JP | 63-238103 | 10/1988 |
| JP | 02133445 | 5/1990 |
| WO | WO 96/40303 | 12/1996 |

OTHER PUBLICATIONS

Kirk–Othmer Encyclopedia of Chemical Technology, vol. 1, 291 (4th ed. 1992).

Kirk–Othmer Encyclopedia of Chemical Technology, vol. 4, 543 (4th ed. 1992).

Kirk–Othmer, Encyclopedia of Chemical Technology, vol. 6, 146 (4th ed. 1992).

Primary Examiner—Mark L Berch
Assistant Examiner—Zachary C. Tucker
(74) Attorney, Agent, or Firm—Stephen W. Buckingham

(57) ABSTRACT

Described are (alkyl,bromo)phenoxy alkyl (meth)acrylate monomers and polymers made therefrom.

5 Claims, No Drawings

BROMINATED MATERIALS

CROSS-REFERENCE RELATED TO OTHER APPLICATIONS

This application is a divisional of application Ser. No. 09/402,850, filed Oct. 7, 1999, now U.S. Pat No. 6,359,170.

FIELD OF THE INVENTION

The invention relates to (alkyl,bromo)phenoxy alkyl (meth)acrylate monomers and polymers made therefrom.

BACKGROUND

Reactive chemical monomers can be used to prepare polymeric materials which have various properties and which are useful for various applications. As one example, monomers having optical properties can generally be used, alone or in combination with other reactive materials, to produce useful products having a high index of refraction, and that are useful to control the flow and intensity of light. To continually improve such products, or the processes for preparing such products, there is an ongoing need to develop new and improved high index of refraction monomeric materials.

Some brominated aromatic (meth)acrylate monomers have been found to be useful as high index of refraction monomers. These monomers can exhibit desirable optical qualities, but generally tend to display relatively high melting points, and therefore exist as solids at temperatures near room temperature (e.g., in the range from about 20 to 30 C.). Often such known brominated monomers have melting points significantly above room temperature. In addition, polymerization of these monomers (by themselves or with other comonomers) can frequently lead to a polymer with a relatively high glass transition temperature (Tg) which can limit the range of application of such monomers.

It would be desirable to identify monomers useful to produce optical materials, where the monomers have physical properties including a relatively high index of refraction, a relatively low melting point in combination with a relatively low room temperature viscosity, and which can be used to prepare polymers (e.g., homopolymers or copolymers) having a relatively low Tg.

SUMMARY OF THE INVENTION

The invention provides (alkyl,bromo)phenoxy alkyl (meth)acrylate monomers. The term (alkyl,bromo)phenoxy alkyl (meth)acrylate is used herein to refer to chemical compounds comprising a (meth)acrylate, a phenoxy ring substituted with at least bromine and an alkyl group, and a divalent alkylene group connecting the (meth)acrylate to the phenoxy ring. Preferred monomers exhibit a relatively high index of refraction; i.e., at least 1.50. Preferred monomers also have a relatively low melting temperature; i.e., below about 60 degrees celsius (60 C.), more preferably below about 35° C. or 30° C., and most preferably exist as a liquid at or near normal room temperature (e.g., 25 C.). In addition, preferred monomers have a relatively low room temperature viscosity, and can be polymerized, either alone or in combination with one or more other comonomers, to prepare polymers with a relatively low glass transition temperature (Tg), e.g., <50 C.

An aspect of the invention relates to (alkyl,bromo) phenoxy alkyl (meth)acrylate monomers such as those having the general formula:

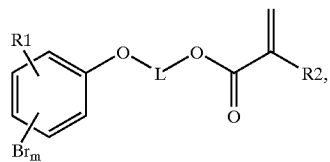

wherein m is from 1 to 4; R2 is hydrogen or methyl, R1 is a straight or branched alkyl having at least two carbon atoms, and L is a straight or branched alkylene.

Another aspect of the invention relates to a polymerizable composition containing an (alkyl,bromo)phenoxy alkyl (meth)acrylate monomer such as that defined directly above. The polymerizable composition can further contain one or more other comonomer.

Yet another aspect of the invention relates to a polymer or polymeric material comprising a chemical segment having the formula:

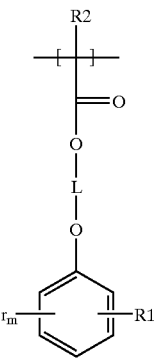

wherein m is from 1 to 4, R2 is —H or methyl, R1 is a straight or branched alkyl having at least two carbons, and L is a straight or branched alkylene. Such a polymer can be prepared by polymerization of the (alkyl,bromo)phenoxy alkyl (meth)acrylate monomer.

As used within the present description, "monomer" refers to a monomer on an individual (i.e., molecular) scale, and also to a composition of such monomers on a macroscopic scale such that the composition can be described as having a physical state of matter (e.g., liquid, solid, etc.) and physical properties (e.g., melting point, viscosity, glass transition temperature (of a polymeric form), and index of refraction).

"Index of refraction," or "refractive index," refers to the absolute refractive index of a material (e.g., a monomer), which is understood to be the ratio of the speed of electromagnetic radiation in free space to the speed of the radiation in that material, with the radiation being of sodium yellow light at a wavelength of about 583.9 nanometer (nm). Index of refraction can be measured by known methods, and is generally measured using an Abbe Refractometer.

"Glass transition temperature," (Tg), is the temperature range over which a thermoplastic polymer changes from a brittle, glass state to a plastic state. Tg can be measured by methods known in the analytical chemistry art, such as the method described in the Examples section below.

"(Meth)acrylate" refers to both acrylate and methacrylate compounds.

DETAILED DESCRIPTION

Monomers of the invention include (alkyl,bromo) phenoxy alkyl (meth)acrylate monomers, wherein the alkyl group includes at least two carbon atoms (also referred to herein as "the monomer" or "the brominated monomer," in both singular and plural forms). The (alkyl,bromo)phenoxy alkyl (meth)acrylate monomer can comprise a (meth) acrylate, a phenoxy ring substituted with substituents comprising bromine and an alkyl group, and a divalent alkylene group connecting the two.

The alkyl group can be straight or branched, and can preferably have from 2 to about 12 carbon atoms, more preferably from about 3 to about 12 carbon atoms. The size, position, and structure of the alkyl group are believed to affect properties of the monomer and polymers prepared therefrom, including the refractive index and viscosity of the monomer, and the refractive index and Tg of a polymer made from the monomer. For example, relatively larger or more branched alkyl groups can provide monomers capable of being polymerized to polymers having relatively lower glass transition temperatures, compared to otherwise similar monomers having fewer carbon atoms or less branching. Additionally, a relatively larger alkyl group can result in a monomer or polymer having a relatively lower index of refraction as compared to a similar monomer having a relatively smaller alkyl group.

The alkylene group can generally be any divalent organic hydrocarbon group. The alkylene group can be straight or branched, and preferred alkylene groups can contain from about 1 to about 12 carbon atoms, more preferably from about 2 to about 6 carbons. The size and chemical structure of the alkylene group can affect the physical properties of the monomer and a polymer prepared therefrom, including the refractive index and viscosity of the monomer and the refractive index and Tg of a polymer prepared from the monomer. A relatively larger alkylene group can result in a monomer or polymer having a relatively lower index of refraction as compared to an otherwise similar monomer having a relatively smaller alkylene group. Relatively larger or more branched alkylene groups can provide a monomer which when polymerized has a relatively lower Tg compared to a polymer prepared from otherwise similar monomers having relatively smaller or less branched alkylene groups.

Bromine substitution can affect the index of refraction of the monomer. It is generally understood that bromine increases the index of refraction of the monomer. Bromine can be substituted on the aromatic portion of the monomer in any available amount or position, and will preferably be present in an amount to provide a monomer having a relatively high index of refraction, preferably at least about 1.50. This can be accomplished, for example, by having at least two bromines directly attached to the aromatic ring.

Often, the position of the bromine can be a function of the materials and process used to prepare the brominated monomer (e.g., as described infra). Also, the position of an alkyl group on the aromatic ring can affect at least in part the position of bromines attached directly to the aromatic ring. If an alkyl group is attached at the 4 position relative to the ester substituent (para-), two bromines can preferably be located at the 2 and 6 position, and, if the alkyl group is at the 2 position (ortho-), bromines are preferably at the 4 and 6 positions.

Examples of useful (alkyl,bromo)phenoxy alkyl (meth) acrylate monomers include those having the structure of formula 1:

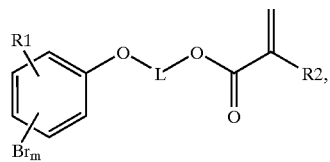

(1)

wherein:

R2 can be hydrogen (—H) or methyl (—CH$_3$);

m can be from about 1 to 4, and is preferably about 2;

L can be a straight chain or branched alkylene group, preferably containing from 1 to about 12 carbon atoms, more preferably from about 2 to about 6 carbon atoms; and R1 can be a straight or branched alkyl having at least 2 carbon atoms, preferably having at least 3 and up to about 12 carbon atoms. R1 can be positioned ortho, meta, or para to the phenoxy oxygen.

The monomer preferably exhibits desired properties of index of refraction, melting point, and viscosity. The monomer preferably exhibits an index of refraction of at least about 1.50. The melting point of the monomer can be below about 60° C., preferably below about 35° C. or 30° C., and most preferably the monomer exists as a liquid at or near normal room temperature. The monomer can have a room temperature viscosity that allows the monomer or a polymerizable composition thereof to be processed, e.g., pumped, circulated, extruded, coated, formed, cured, or otherwise handled, at or near room temperature. Although viscosities outside of the following ranges can be useful, preferred viscosities of the monomer can be in the range from about 20 to 5000 centipoise (cps), more preferably from about 50 to 1000 cps, as measured at 23 C. Also, preferred monomers can be polymerized or copolymerized to provide polymeric materials having relatively low Tg, e.g., below about 50 C. Particularly preferred monomers have both a relatively high index of refraction (e.g., greater than about 1.50), and can produce a polymer having a relatively low Tg (e.g., below about 50 C.).

Examples of useful monomers of the invention include monomers wherein R1 is located ortho to the phenoxy oxygen, as illustrated by formula 2:

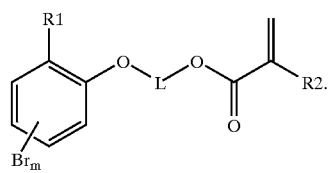

(2)

In formula 2, R2, m, L, and R1 are as defined supra. In a particularly preferred embodiment, bromine atoms are located at the 4 and 6 positions on the phenoxy ring, ortho and para to the phenoxy oxygen atom, as illustrated by formula 3:

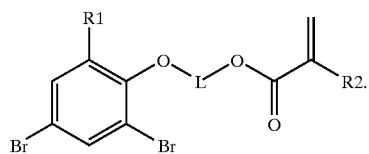
(3)

Particularly preferred monomers of formula 3 include 4,6-dibromo-2-alkyl phenoxy alkylene (meth)acrylates wherein the R1 alkyl has from 3 to 4 carbons, including monomers of the types shown in formulas 4 and 5, wherein R2 and L, are as defined:

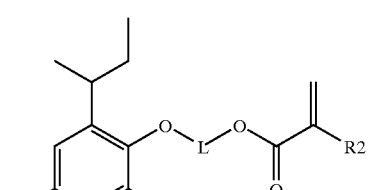
(4)

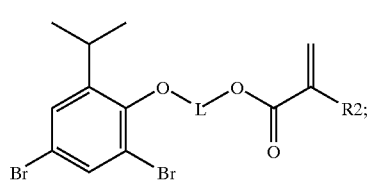
(5)

With R2 as hydrogen and L as ethylene these become 2-(4,6-dibromo-2-sec-butyl penoxy) ethyl acrylate:

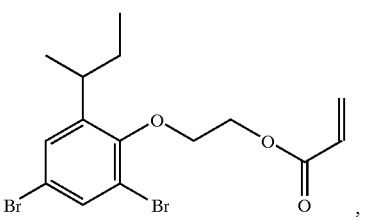
(4.1)

and 2-(4,6-dibromo-2-isopropyl phenoxy)ethyl acrylate:

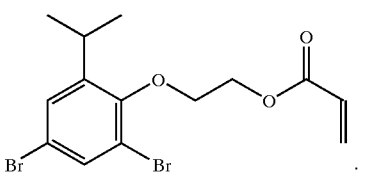
(5.1)

With R2 as hydrogen and L as hexylene these become 6-(4,6-dibromo-2-sec-butyl penoxy) hexyl acrylate:

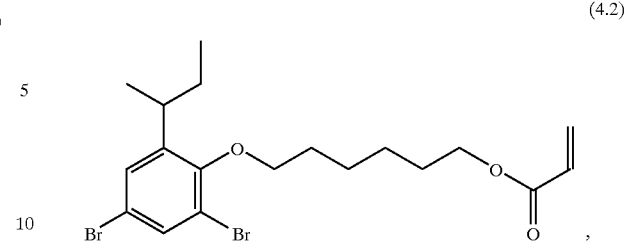
(4.2)

and 6-(4,6-dibromo-2-isopropyl phenoxy) hexyl acrylate:

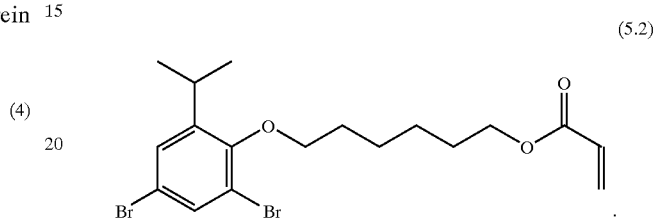
(5.2)

(Alkyl,bromo)phenoxy alkyl (meth)acrylate monomers of the invention can be prepared by methods generally useful in preparing substituted (e.g., brominated) phenoxy compounds and (meth)acrylate monomers. Such methods are well known in the organic chemistry art.

As an example of one method of preparing the monomers of the invention, the following steps can be used. First, an alkyl-substituted phenol (alkylphenol) can be brominated to produce a brominated alkylphenol, as desired to prepare the desired brominated monomer.

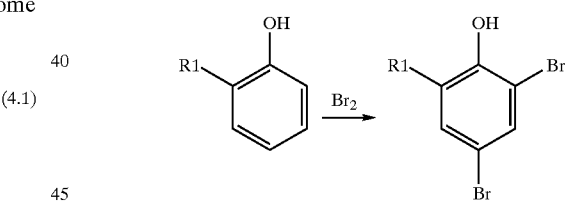

Alkylphenols are commercially available from Schenectady International Inc., Chemical Division, Schenectady, N.Y. Alkylphenols can be brominated by methods that are known in the organic chemistry art, and as described, for example, in the Kirk-Othmer Encyclopedia of Chemical Technology, Volume 4, 543 (4$^{th}$ ed. 1992).

The brominated alkylphenol can be alkylated by known methods to produce an (alkyl,bromo)phenoxy alkanol compound.

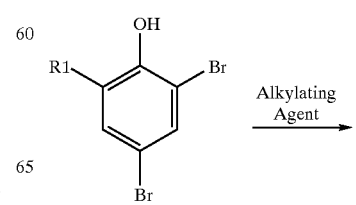

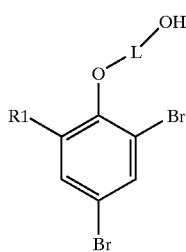

Alkylation methods are known in the chemical art, and are generally accomplished by introducing an alkylating agent, for example any one of an alkylene carbonate (e.g., ethylene carbonate), a chloroalkanol (e.g., chloroethanol) or an alkylene oxide (e.g., ethylene oxide) to the brominated alkylphenol under proper conditions to allow the alkylating agent to react with the phenol alcohol and cause alkylation. See, e.g., U.S. Pat. No. 2,448,767; and Kirk-Othmer, Encyclopedia of Chemical Technology, Vol. 6, 146 (4$^{th}$ ed. 1992).

Also using methods known in the organic chemistry art, the resulting (alkyl,bromo)phenoxy alkanol compound can be esterified to give a brominated (meth)acrylate monomer:

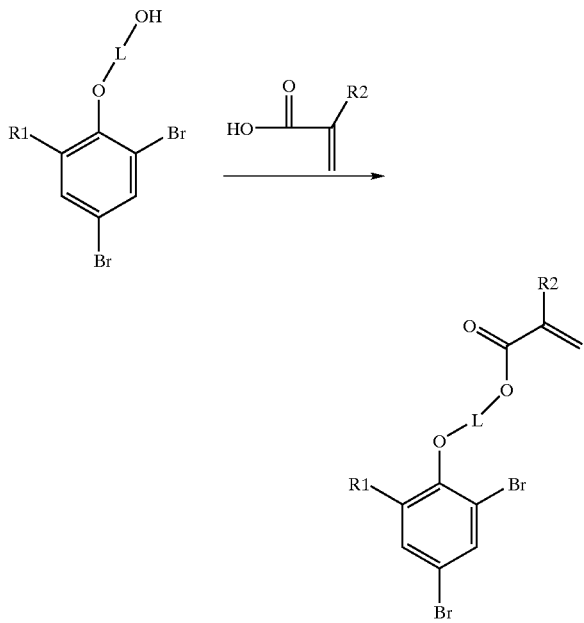

Esterification reactions are well known in the chemical art, and are described, for example, in the Kirk-Othmer Encyclopedia of Chemical Technology, vol. 1, 291 (4$^{th}$ ed. 1992).

A preferred step in the preparation of the brominated monomer can be a purification step. Purification can be accomplished by any method known in the organic chemistry art, including methods of chromatography and distillation. For some brominated monomers, for example those that might suffer from thermal breakdown at elevated temperatures, it can be preferred to purify the monomers using ultra-high vacuum continuous distillation methods. These processes can be accomplished at pressures in the range from about 1 to 1000 micron mercury (Hg), and temperatures in the range from about 100 to 200 C.

The brominated monomer of the invention, alone or in combination with other materials such as other unsaturated polymerizable comonomers, can be included in a polymerizable composition that can be polymerized or co-polymerized to produce useful polymers or copolymers. As used within the present description the term "polymerizable" refers to chemical compounds such as monomers and oligomers, etc., and chemical compositions, capable of polymerizing or copolymerizing (e.g., via unsaturated moieties) to produce a higher molecular weight material such as an oligomer, polymer, prepolymer, or polymeric material. The terms "polymer" and "polymeric material" are used interchangeably to refer to materials prepared from the reaction of one or more polymerizable materials, e.g., one or more polymerizable monomer, oligomer, polymer, or prepolymer, etc. to produce a dimer, trimer, oligomer, copolymer, homopolymers, etc.

Useful comonomers to be reacted with acrylic monomers such as the brominated monomer described herein are known in the organic chemistry art, and can include any of a number of known and useful polymerizable moieties, e.g., vinyl, (meth)acrylate, N-vinyl, acrylic acid, methacrylic acid, allyl, acrylamide, acrylonitrile, etc. The comonomer can be mono- or multifunctional with respect to the unsaturated moiety, and where multifunctional, the unsaturated moieties need not be of identical chemistry.

Specific types of comonomer useful in the polymerizable composition can include the class of (meth)acrylate-functional comonomers such as butyl (meth)acrylate, as well as vinyl comonomers such as methyl styrene. The particular comonomers included in any given polymerizable composition, their molecular weight or weights, and the included amounts of each, can be chosen according to various factors such as the desired nature and properties of the polymerizable composition and the desired properties of the polymer or polymeric material to be prepared therefrom (e.g., index of refraction, glass transition temperature, melting point, viscosity, etc., of the polymerizable composition or polymeric material).

The polymerizable composition can also contain other ingredients that, as will be appreciated by those skilled in the art of polymeric materials, can be useful in such a polymerizable composition. For example, the polymerizable composition might contain a crosslinking agent, one or more surfactants, pigments, fillers, polymerization inhibitors, or other ingredients that can be useful within a polymerizable composition or an optical product. Such ingredients can be included in the composition in amounts known to be effective for their respective purposes.

A crosslinking agent can be useful to increase the glass transition temperature of the polymer resulting from crosslinking the polymerizable composition. Glass transition temperature of a composition can be measured by methods known in the art, such as Differential Scanning Calorimetry (DSC), modulated DSC (MDSC), or Dynamic Mechanical Analysis (DMA).

Polymeric beads, inorganic fillers, and/or pigments can be added to the polymerizable composition in order to improve processing, to impart slip and scratch resistance to the polymerized material, or to affect optical properties of the polymerized material. Examples of useful polymeric beads include those made of polystyrene, polyacrylates, copolymers of styrene and acrylates, polyethylene, polypropylene, polytetrafluoroethylene, or combinations thereof. Examples of inorganic fillers and pigments include solid or hollow glass beads, silica, zirconia, aluminum trihydroxide, and titanium dioxide.

The polymerizable composition can preferably have a room temperature viscosity that allows the polymerizable composition to be processed, e.g., pumped, circulated, extruded, coated, formed, cured, or otherwise handled, at or near room temperature. Although viscosities outside of the following ranges can also be useful, preferred viscosities of the polymerizable composition can be in the range from about 20 to 5000 centipoise (cps), more preferably in the range from about 50 to 1000 cps, as measured at 23 C.

Polymerization of the composition can be accomplished by known and usual means, such as heating in the presence of a free-radical initiator, irradiation with electromagnetic radiation such as ultraviolet or visible light in the presence of suitable photoinitiators, and by electron beam. For reasons of convenience and production speed, a preferred method of polymerization might be by irradiation with ultraviolet or visible light in the presence of photoinitiator.

Polymeric materials (i.e., homopolymers or copolymers) prepared from the brominated monomer can exhibit a relatively low Tg, e.g., below about 50C.

The invention will be more fully appreciated with reference to the following non-limiting examples in which the reaction components are given as grams used or as weight percents (wt %), based on the total weight of the reaction mixtures which are nominally 100 weight %. Dimensions in English units are nominal and conversion to metric units is approximate.

EXAMPLE 1

Synthesis of 2-(4,6-dibromo-2-sec-butyl phenoxy) ethyl acrylate

A. Preparation of 4,6-dibromo-2-sec-butyl phenol (DBsBP) (bromination)

In a 12 liter round bottom flask equipped with a mechanical stirrer, condenser, nitrogen cap, addition funnel and temperature probe, 1500 g (grams) of 2-sec-butylphenol was mixed with 4500 g of deionized water. The mixture was stirred with a mechanical mixer and purged with nitrogen for about 10 minutes. 3319 g bromine was added to the mixture drop-wise through the addition funnel. The temperature was maintained at about 30° C. or less using an ice bath. Following addition of the bromine, the reaction mixture was stirred for one hour at room temperature. Reaction completion was determined by gas chromatography, by monitoring the disappearance of the starting material, 2-sec-butylphenol, and of monobrominated species.

Upon completion of the reaction, 3960 g of ethyl acetate was added. The mixture was stirred for 15 minutes and then allowed to phase split. The bottom (aqueous) layer was removed and 2686 g of a 13 wt % aqueous sodium hydrosulfite solution was added. The mixture was stirred well and then allowed to phase split. The bottom (aqueous) layer was removed and 2760 g of a 15 wt % aqueous sodium carbonate solution was added. The mixture was stirred well and then allowed to phase split. The bottom (aqueous) layer was removed and solvent was stripped from the top layer using a rotary evaporator. This procedure provided approximately 2647 g of DBsBP.

B. Preparation of 2-(4,6-dibromo-2-sec-butyl phenoxy) ethanol (alkylation)

A 500 ml round bottom flask was equipped with a magnetic stirrer, condenser and temperature probe. 40 g of the 4,6-dibromo-2-sec-butylphenoxy, 12.5 g ethylene carbonate and 13.1 g triethylamine were added to the flask. The mixture was heated to reflux (~120 C.) and held at that temperature for about 24 hours. At this point, gas chromatograph analysis showed only 0.9% residual starting material, so the reaction was cooled to room temperature. 170 g t-butyl methyl ether was added, then 20.1 g of 37% HCl in 150 g of DI water was added. The mixture was shaken well and allowed to phase split and the lower aqueous phase removed. The mixture was then washed with a solution of 150 g water and 15 g of sodium carbonate and the lower aqueous phase was removed. The solvent was remove using a rotary evaporator to yield about 40 grams of dark intermediate product. This product batch distilled using a 163° C. pot, 115° C. overhead condenser and 0.2 mm Hg vacuum to yield the yellow desired product, 2-(4,6-dibromo-2-sec-butyl phenoxy) ethanol.

C. Preparation of 2-(4,6-dibromo-2-sec-butyl phenoxy) ethyl acrylate (esterification)

A 500 ml round bottom flask was equipped with a mechanical stirrer, Dean-Stark trap, condenser, and temperature probe. 25 g of 2-(4,6-dibromo-2-sec-butylphenoxy) ehtanol, 125 g of toluene, 0.58 g of p-toluene sulfonic acid, 5.5 g of acrylic acid and ~200 ppm each of methyl hydroquinone and hydroquinone were mixed together in the flask. The mixture was heated to reflux to azeotrope out the water generated during esterification. After 5 hours, gas chromatography analysis showed the reaction to be substantially complete (>98%). The reaction mixture was cooled washed three times: first with a solution of HCl in water, then with a solution of $NaCO_3$ in water and finally with a solution of NaCl in water and the toluene was then stripped in vaccuo. The product was purified using continuous distillation on a rolled film evaporator (available from UIC Inc. of Joliet, Ill.) at the following conditions: 1 micron Hg vacuum and 130° C. to obtain the product with >98% purity by NMR.

EXAMPLE 2

Preparation of 6-(4,6-dibromo-2-isopropyl phenoxy) hexyl acrylate

A. Preparation of 4,6-dibromo-2-isopropyl phenol (DBiPP) (bromination)

The procedure describing the preparation of DBsBP was followed using 1400 g of 2-isopropylphenol instead of the 2-sec-butylphenol, 4630 g of water, 3417 g of bromine, 4075 g of ethyl acetate, 2765 g of 13% (w/w) aqueous sodium hydrosulfite and 2842 g of 15% (w/w) aqueous sodium carbonate to produce 2556 g of DBiPP.

B. Preparation of 6-(4,6-dibromo-2-isopropyl phenoxy) hexanol (alkylation)

A 12 liter, four neck, round bottom flask was set up with a mechanical stirrer, condenser, temperature probe and addition funnel in a cooling bath. 800 grams of 4,6-dibromo-2-isopropyl phenol (DBiPP) was added to the flask along with 4902 grams of deionized water and 408 grams of sodium iodide. Using the addition funnel, 435 grams of a 50% sodium hydroxide solution was added while maintaining the temperature below 25 C. The cooling bath was then removed and the reaction mixture was heated to reflux (100C.). Using a clean addition funnel, 744 grams of 6-chlorohexanol was added over 1 hour and 30 minutes. The reaction was mixed two more hours at which point gas chromatography (GC) analysis indicated 0.3% of the starting DBiPP remained unreacted. The solution was cooled and left at room temperature (22–25 C) overnight.

4196 grams of ethyl acetate was added to the reaction flask and mixed for 10 minutes (t-butyl methyl ether or other suitable organic solvent may be used). The mixture was allowed to phase split. The bottom aqueous layer was removed by vacuum and the pH was recorded at 11. The washing step was repeated a second time using a solution of 27 grams of 37% HCl in 980 grams of deionized water. The aqueous phase that was removed had a pH of 1. The washing step was repeated a third time using 980 grams of a 3% (w/w) aqueous sodium carbonate solution. Again the aqueous phase was removed and the pH was recorded at 11. The final washing was done with a 4.7% (w/w) aqueous solution of sodium chloride (982 grams). The aqueous phase was again removed by vacuum. The organic phase filtered and concentrated on a rotary evaporator using a water aspirator. Residual solvent was removed using a vacuum pump while stirring the concentrate with a magnetic stirrer. 1250 grams of a yellow liquid was obtained. The yellow liquid was purified by continuous distillation using a rolled film evaporator. First 6-chlorohexanol and 6-iodohexanol were removed at the following conditions: 130° C. oil bath and 5–20 microns Hg vacuum. The residue was then continuously distilled on the rolled film evaporator using the following conditions: 130° C. oil bath and 1 micron Hg vacuum. 832 grams of the water white alkylated product (6-(4,6-dibromo-2-isopropyl phenoxy) hexanol) was recovered. It can be noted here that optionally, a wiped film evaporator can be used in place of the rolled film evaporator.

C. Preparation of 6-(4,6-dibromo-2-isopropyl phenoxy) hexyl acrylate (esterifilcation)

A five liter, four neck round bottom flask was equipped with a mechanical stirrer, Dean Stark trap, condenser and temperature probe. The flask was charged with 600 grams of 6-(4,6-dibromo-2-isopropyl phenoxy) hexanol; 2805 grams of toluene; ~200 ppm each of methyl hydroquinone and hydroquinone; 15.2 grams p-toluene sulfonic acid and 131 grams acrylic acid. This mixture was heated to reflux with stirring to azeotrope the water. After six hours of refluxing, 30 ml of water had been removed and 99.2% of the 6-(4,6-dibromo-2-iso-propyl phenoxy) hexanol had been converted to the 6-(4,6-dibromo-2-iso-propyl phenoxy) hexyl acrylate based on gas chromatography (GC) analysis. The solution was then cooled and allowed to mix overnight.

828 grams of a 0.27% HCl solution was added to the reaction flask and mixed for five minutes. The mixture was allowed to phase split and the aqueous bottom phase (pH=1) was removed by vacuum. The washing was repeated by adding 903 grams of an 8.9% (w/w) aqueous solution of sodium carbonate. The aqueous phase was removed after phase separation. A third wash was done using 867 grams of a 5.1 % (w/w) aqueous sodium chloride solution. The aqueous phase was again removed by vacuum. The organic phase was filtered and concentrated on a rotary evaporator using a water aspirator. Residual solvent was removed using a vacuum pump while stirring the concentrate with a magnetic stirrer. 650 grams of a hazy, light yellow liquid was obtained. The yellow liquid was then purified by continuous distillation in a rolled film evaporator using the following conditions: 175° C. oil bath and 1 micron Hg vacuum to give the water white product. NMR analysis indicated a 98.8% purity prior to distillation and a purity of >99% in the distilled product, 6-(4,6-dibromo-2-iso-propyl phenoxy) hexyl acrylate.

EXAMPLE 3

Preparation of a mixture of 2-(4,6-dibromo-2-sec-butyl phenoxy) 2-methyl ethyl acrylate and 2-(4,6-dibromo-2-sec-butyl phenoxy) 1-methyl ethyl acrylate A. Preparation of 4,6-dibromo-2-sec-butyl phenol (DBsBP) (bromination)

4,6-dibromo-2-sec-butyl phenol (DBsBP) was prepared according to the procedure described in Example 1.

B. Preparation of a mixture of 2-(4,6-dibromo-2-sec-butyl phenoxy) 2-methyl ethanol and 2-(4,6-dibromo-2-sec-butyl phenoxy) 1-methyl ethanol (alkylation)

A 500 ml round bottom flask was equipped with a magnetic stirrer, condenser and a temperature probe. The flask was charged with 60 grams of 4,6-dibromo-2-sec-butyl phenol (DBsBP), 21.9 grams of propylene carbonate, and 19.7 grams of triethylamine. The mixture was heated to reflux (120 C.) and held at that temperature for about 24 hours. The mixture was cooled to room temperature and the flask was charged with 170 grams of t-butyl methyl ether. 170 grams of a 4.3% aqueous solution of HCl was added to the reaction flask and mixed. The mixture was allowed to phase separate and the aqueous phase was removed. 165 grams of a 9.1% aqueous solution of sodium carbonate was then added to the flask, mixed and allowed to phase separate. The aqueous phase was again removed. The ether solvent was then removed using a rotary evaporator. 68 grams of dark alkylated product was recovered. $^{13}C$ NMR analysis indicated the recovered product to be predominately a mixture of 2-(4,6-dibromo-2-sec-butyl phenoxy) 2-methyl ethanol and 2-(4,6-dibromo-2-sec-butyl phenoxy) 1-methyl ethanol.

C. Preparation of a mixture of 2-(4,6-dibromo-2-sec-butyl phenoxy) 2-methyl ethyl acrylate and 2-(4,6-dibromo-2-sec-butyl phenoxy) 1-methyl ethyl acrylate (esterification)

A five liter, four neck round bottom flask was equipped with a mechanical stirrer, Dean Stark trap, condenser and temperature probe. The flask was charged with 25 grams of the intermediate alkylated product from example 3B, 125 grams of toluene, 5.9 grams of acrylic acid, 0.58 grams p-toluene sulfonic acid, and about 200 ppm each of methyl hydroquinone and hydroquinone. The mixture was heated to reflux to azeotrope out the water generated during esterification. Gas chromatography analysis after three hours of reflux showed only slight conversion. The toluene was then stripped using a rotary evaporator and an equal amount of xylenes were added back to the flask. This mixture was then heated to reflux (~140° C.) to azeotrope out water. After one hour, gas chromatography showed 33% conversion of the alcohol. Acrylic acid (2 grams) was added to the flask and reflux was continued an additional an additional two hours. At this point, the conversion was >90%. The reaction mixture was then cooled and washed as described in Section 1C above, and the xylenes were stripped using a rotary evaporator. The crude product remaining in the evaporator flask was passed through a flash chromatography column using methylene chloride to isolate the desired product. The solvent was again removed using a rotary evaporator. Residual solvent was removed using a vacuum pump while stirring the concentrate with a magnetic stirrer. $^{13}C$ NMR analysis of the product showed a mixture of 2-(4,6-dibromo-2-sec-butyl phenoxy) 2-methyl ethyl acrylate (~77%) and 2-(4,6-dibromo-2-sec-butyl phenoxy) 1-methyl ethyl acrylate (~11%).

EXAMPLES 4–16

Using bromination, alkylation and esterification steps similar to those described in Examples 1 to 3, a variety of (alkyl,bromo)phenoxy alkyl (meth)acrylate monomers were prepared. By using appropriate starting materials, stoichiometric quantities, and the methods described in Examples 1–3, one skilled in the art of organic chemistry could prepare the materials of Examples 4–16 in Table 1.

TABLE 1

Synthesized Monomers

| Example | Name |
|---|---|
| 1 | 2-(4,6-dibromo-2-sec-butyl phenoxy) ethyl acrylate |
| 2 | 6-(4,6-dibromo-2-isopropyl phenoxy) hexyl acrylate |
| 3 | 2-(4,6-dibromo-2-sec-butyl phenoxy) 2-methyl ethyl acrylate and 2-(4,6-dibromo-2-sec-butyl phenoxy) 1-methyl ethyl acrylate |
| 4 | 6-(4,6-dibromo-2-sec-butyl phenoxy) hexyl acrylate |
| 5 | 2-(4,6-dibromo-2-isopropyl phenoxy) ethyl acrylate |
| 6 | 6-(4,6-dibromo-2-dodecyl phenoxy) hexyl acrylate |
| 7 | 2-(4,6-dibromo-2-dodecyl phenoxy) ethyl acrylate |
| 8 | 2-(2,6-dibromo-4-nonyl phenoxy) ethyl acrylate |
| 9 | 2-(2,6-dibromo-4-dodecyl phenoxy) ethyl acrylate |
| 10 | 6-(4,6-dibromo-2-sec-butyl phenoxy) hexyl methacrylate |
| 11 | 6-(4,6-dibromo-2-isopropyl phenoxy) hexyl methacrylate |
| 12 | 2-(4,6-dibromo-2-sec-butyl phenoxy) ethyl methacrylate |
| 13 | 2-(4,6-dibromo-2-isopropyl phenoxy) ethyl methacrylate |
| 14 | 2-(4,6-dibromo-2-dodecyl phenoxy) ethyl methacrylate |
| 15 | 2-(2,6-dibromo-4-nonyl phenoxy) ethyl methacrylate |
| 16 | 2-(2,6-dibromo-4-dodecyl phenoxy) ethyl methacrylate |

Experimental Methods
Homopolymerization

Homopolymers of several of the above noted monomers were prepared by combining 2 grams of monomer with 10 grams of ethyl acetate solvent and 0.006 grams of Vazo 64 or Vazo 88 initiatior (available from Dupont) in a 4 ounce (118.3 ml) glass bottle. The bottle was purged for one minute with nitrogen at a flow rate of one liter per minute. The bottle was sealed and then palced in a rotating water bath at 55° C. (65° C. if Vazo 88 initiator was used) for 24 hours to effect essentially complete polymerization. The homopolymer was recovered for Tg analysis by evaporating the solvent at 105 C.

Glass Transition (Tg)

Glass transition temperatures (Tg) were determined using a differential scanning calorimeter (DCS-7) manufactured by Perkin Elmer, Norwalk, Conn. A 10 mg polymer sample was heated at a rate of 20 C./minute, cooled at a rate of 40 C./minute and then reheated at 20 C./minute. The Tg was calculated nd heating cycle.

Viscosity

Steady shear viscosity measurements were made at 25° C. using a 40 mm parallel plate fixture on Rheometrics Stress Rheometer (DSR) which is a commercially available instrument sold by Rheometrics, Scientific, One Rd., Piscataway, N.J. 08854. The sample of monomer was sandwiched two plates and squeezed out till a gap setting of 0.45 to 0.5 mm was achieved. The excess material was cleaned out and the sample was then subjected to a set of predetermined shear rates. At each shear rate, the viscosity measurement was made when the torque was at steady state. Analysis indicated the viscosity to be independent of the shear rate. The viscosity was reported in Table 2 in cps).

Refractive Index

The refractive index of resin compositions and cured films were measured using an Abbe Refractometer, made by Erma Inc. of Tokyo Japan and distributed by Fisher Scientific.

TABLE 2

Properties of Monomers and Homopolymers

| Example | Monomer Refractive Index | Monomer Viscosity, (cps) | Tg of Homopolymer (° C.) |
|---|---|---|---|
| 1 | 1.5455 | 120 | 33 |
| 2 | 1.5340 | 90 | −10 |
| 3 | 1.5432 | | |
| 4 | 1.5265 | 90 | −20 |
| 5 | 1.5490 | 120 | |
| 6 | 1.5135 | 80 | |
| 7 | 1.5210 | 80 | |
| 8 | 1.5355 | ~1000 | |
| 9 | 1.5280 | ~1000 | |
| 10 | 1.5300 | ~100 | |
| 11 | 1.5335 | ~100 | 7 |
| 12 | 1.5460 | 120 | 39 |
| 13 | 1.5470 | 120 | |
| 14 | 1.5120 | Solid | |
| 15 | 1.5330 | ~1000 | |
| 16 | 1.5280 | ~1000 | |

What is claimed is:

1. A polymerizable composition comprising monomer of the formula:

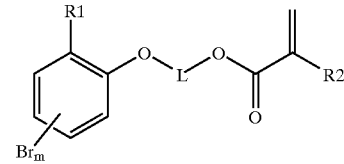

wherein m is from 1 to 4, R2 is H or methyl, R1 is a straight or branched alkyl having at least 2 carbons, and L is a straight chain or branched alkylene.

2. The polymerizable composition of claim 1 wherein the composition is liquid at room temperature.

3. The polymerizable composition of claim 1 wherein the composition has a room temperature viscosity that allows the composition to be processed at room temperature.

4. The polymerizable composition of claim 1 having a viscosity in the range from about 20 to about 5000 centipoise.

5. The polymerizable composition of claim 1 having an index of refraction of at least 1.50.

* * * * *